United States Patent [19]

Hannah

[11] 4,283,402
[45] Aug. 11, 1981

[54] 6-N-HETEROCYCLYL-3-TETRAZOLYL-PENICILLINS

[75] Inventor: John Hannah, Matawan, N.J.

[73] Assignee: Merck & Co., Inc., Rahway, N.J.

[21] Appl. No.: 62,828

[22] Filed: Aug. 1, 1979

[51] Int. Cl.³ .......................................... C07D 402/02
[52] U.S. Cl. .................................. 424/256; 424/267;
424/263; 424/273 R; 424/273 B; 424/270;
424/251; 546/112; 546/138; 546/270; 546/272;
260/245.2 R
[58] Field of Search ..................... 260/245.2; 424/256,
424/270, 263, 267; 546/112, 270, 138, 272, 280,
276

[56] References Cited

U.S. PATENT DOCUMENTS 4,081,455  3/1978  Kuhla .............................. 260/245.2
4,143,039  3/1979  Barth .................................. 424/270

Primary Examiner—Nicholas S. Rizzo
Attorney, Agent, or Firm—Frank M. Mahon; Hesna J. Pfeiffer

[57] ABSTRACT

This invention relates to a new class of penicillins (I) and their pharmaceutically acceptable salts which are useful as antibiotics:

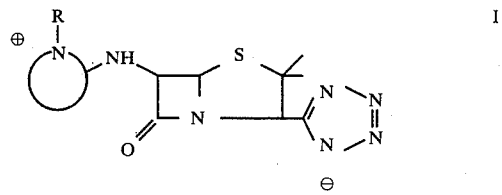

wherein the stylized radical (hereafter referred to as R'):

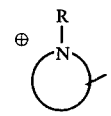

attached to the 6-amino nitrogen moiety of the penicillin nucleus represents a mono- or polycyclic N-containing heterocyclic group; and R is, inter alia, hydrogen, substituted and unsubstituted: alkyl, aryl, alkenyl, heterocyclylalkyl, heterocyclylalkenyl, aralkenyl, aralkyl, —NR₂, COOR, CONR₂,—OR, or CN.

4 Claims, No Drawings

6-N-HETEROCYCLYL-3-TETRAZOLYL-PENICILLINS

BACKGROUND OF THE INVENTION

This invention relates to a new class of penicillins (I) and their pharmaceutically acceptable salts which are useful as antibiotics:

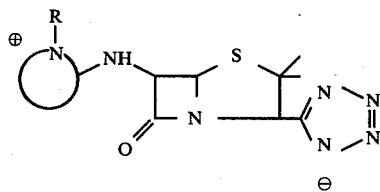

wherein the stylized radical (hereafter referred to as R'):

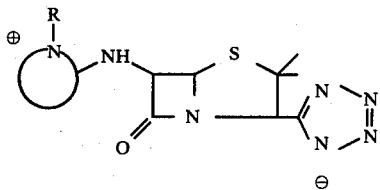

attached to the 6-amino nitrogen moiety of the penicillin nucleus represents a mono- or polycyclic N-containing heterocyclic group; and R is, inter alia, hydrogen, substituted and unsubstituted: alkyl, aryl, alkenyl, heterocyclylalkyl, heterocyclylalkenyl, aralkenyl, aralkyl, $-NR_2$, COOR, $CONR_2$, $-OR$ or CN. The heterocyclic radical, R', is further defined below.

This invention also relates to processes for the preparation of such compounds (I); pharmaceutical compositions comprising such compounds; and to methods of treatment comprising administering such compounds and compositions when an antibiotic effect is indicated.

There is a continuing need for new antibiotics. For unfortunately, there is no static effectiveness of any given antibiotic because continued wide scale usage selectively gives rise to resistant strains of pathogens. In addition, the known antibiotics suffer from the disadvantage of being effective only against certain types of microorganisms. Accordingly, the search for new antibiotics continues.

Thus, it is an object of the present invention to provide a novel class of antibiotics which are useful in animal and human therapy and in inanimate systems. These antibiotics are active against a broad range of pathogens which representatively include both gram positive bacteria such as *S. aureus, Strep. pyogenes,* and *B. subtilis,* and gram negative bacteria such as *E. coli,* Pseudomonas, *Proteus morganii,* Serratia, and Klebsiella. Further objects of this invention are to provide chemical processes for the preparation of such antibiotics and their non-toxic pharmaceutically acceptable salts and esters; pharmaceutical compositions comprising such antibiotics; and to provide methods of treatment comprising administering such antibiotics and compositions when an antibiotics effect is indicated.

DETAILED DESCRIPTION OF THE INVENTION

The compounds of the present invention are prepared by reacting an appropriately substituted 6-amino-3-(5-tetrazolyl)penam starting material (1) [see U.S. Pat. No. 4,143,039] with a chosen electrophilic N-heterocyclic reagent (2 or 3) calculated to provide the species of the present invention I. The following diagram conveniently summarizes this process and introduces the precise identity of such electrophilic reagents and the nature of the products of this reaction (I, above).

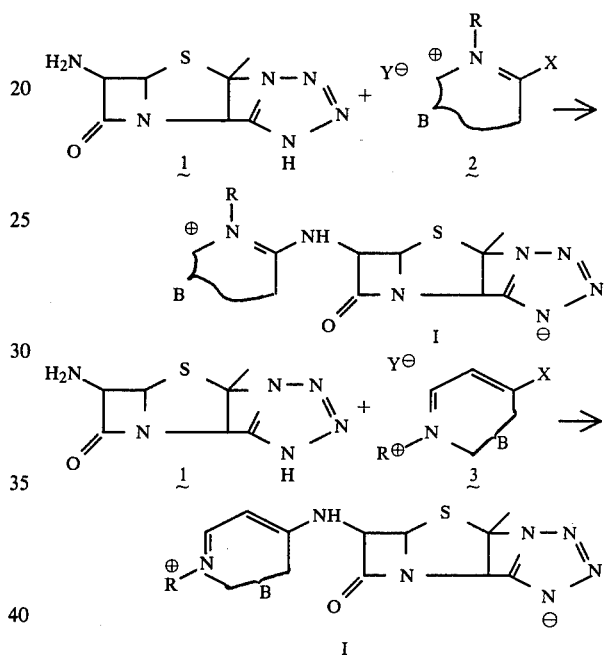

wherein:
B is, inter alia, the residue of a 5-, or a 6-membered aromatic heterocycle; or a 5,5-, 6,5-; or 6,6-bicyclic aromatic heterocycle; wherein the additional ring atoms are chosen either entirely as carbon, or include one or more atoms selected from S, N and O. The carbon and nitrogen atoms of any such ring may carry substituents such as substituted and unsubstituted: alkyl and alkenyl having 1–6 carbon atoms, phenyl, phenylalkyl having 1–6 carbon atoms in the alkyl moiety, 5- or 6-membered heterocyclyl wherein the hetero atom or atoms are selected from O, N or S, $-OR_2$, $-NR_2$, $-COOR$, $-CONR_2$, $-CN$, halo, $-SR$, $-SO.R_3$, $-SO_2R$, $-NHCONH_2$, $-SO_3R$, $-SO_2NR_2$ (R is defined immediately below),

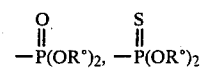

($R°$ is hydrogen or alkyl having 1–6 carbon atoms); wherein the substituent or substituents are selected from halogen such as chlorine or fluorine, hydroxyl, phenyl, alkyl, alkoxyl, carboxyl and phenylalkyl (each alkyl having 1–6 carbon atoms); R is selected from H; substituted and unsubstituted: alkyl having 1–10 carbon atoms, alkenyl having 2–10 carbon atoms, phenyl, phenylalkyl, phenylalkenyl having 7–12 carbon atoms, 5-or 6-membered heterocyclylalkyl wherein the hetero atom or atoms are selected from O, N or S and the alkyl has 1–6 carbon atoms, NR$_2$, OR, COOR, CN, and CONR$_2$ (R is defined here); wherein the substituent or substituents on R are selected from halogen such as chloro and fluoro, hydroxyl, OR, NR$_2$, COOR, CONR$_2$, CN,

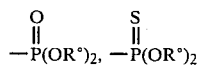

—SR, —SO.R, —SO$_2$R, (R° is hydrogen or alkyl having 1–6 carbon atoms), and alkyl having 1–6 carbon atoms;

R and B together may be joined to yield 6,5- and 6,6-bicyclic heterocycles in which the N$^\oplus$ is at a bridgehead;

X is a leaving group such as halogen, preferably fluorine; other leaving groups include: OCH$_3$, SCH$_3$; OSO$_2$OCH$_3$ OSO$_2$OCF$_3$,

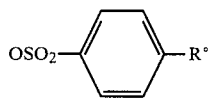

(R° is hydrogen or C$_{1-6}$ alkyl)

Y is a non-critical counter anion and representatively is: Cl$^\ominus$, Br$^\ominus$, I$^\ominus$,

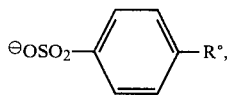

$^\ominus$OSO$_2$OR°, BF$_4^\ominus$, ClO$_4^\ominus$ and the like; wherein R° is H, loweralkyl or phenyl.

In general words relative to the above reaction diagram, the starting material 1 or a salt thereof in a solvent such as water at pH 7 to 8, tetrahydrofuran (THF), dimethylformamide (DMF) or the like or aqueous mixtures thereof (ideally such nonaqueous systems contain a base such as triethylamine, methyldiisopropylamine, or the like, to neutralize the acid HX produced by the addition/elimination reaction) is treated with a stoichiometric to four-fold excess of the illustrated electrophilic reagent (2 or 3) calculated to provide the desired product. Typically, the reaction is conducted at a temperature of from 0° to 40° C. and is accomplished within 1 to 4 hours. As demonstrated by the following examples, there are no undue criticalities in the parameters of reaction. More specifically, relative to the above reaction scheme, a set of representative conditions may be recited to illustrate a convenient preparation of the compounds of the present invention (I); such recitation, however, is solely for purposes of demonstration and is not to be construed as introducing any undue criticalities of reaction.

Standard Reaction Conditions

Using a pH meter coupled to an automatic burette containing 1.0 to 2.5 N aqueous sodium hydroxide, a magnetically stirred suspension of the starting penam (1) in water is solubilized at pH 7 to pH 7.5 at 20° C.

The heterocyclic reagent (stoichiometric to two-fold excess) is dissolved in water at 20° C. and added to the above solution. Alkali is automatically added to maintain the selected pH in the range 7 to 7.5, the rate of addition being a measure of the extent of reaction. The reaction may also be monitored by removing aliquots at timed intervals for analysis. A particularly suitable analytical scheme is liquid chromatography, for example, high pressure liquid chromatography (HPLC) over a reverse phase column of octadecylsilane (ODS) bonded to silica, using a U.V. detector and aqueous THF (tetrahydrofuran) solution (1 to 30%) as the mobile phase.

The reaction typically takes from 15 minutes to 5 hours at 20° C. The resulting reaction solution at pH 7 is worked up by partition chromatography over a column of Amberlite XAD-2 resin, eluting with aqueous THF solutions (up to 20%) and monitoring the fractions by HPLC as above. However, with the increasing availability of large scale ODS silica columns, the preferred method of product isolation is by preparative reverse phase HPLC directly on the reaction solution at pH 7. The appropriate fractions are combined, evaporated to small volume and lyophilized to yield the product, which is conveniently characterized by I.R., U.V., NMR., and analytical HPLC.

In certain cases, the products are sufficiently insoluble in water to separate from the reaction solution at pH 7, and may be isolated simply by filtration.

Finally, a special circumstance should be mentioned. In the basic reaction, first described, the condensation of the penam starting material and the reagent of choice does not occur readily when the group, R, attached directly to the ring nitrogen of the reagent is hydrogen In such circumstance, it is preferred to employ a quaternized ring nitrogen prior to reaction. The quaternizing group may be removed after the amino heterocycle bond has been formed to yield species of the present invention, I, wherein R is hydrogen:

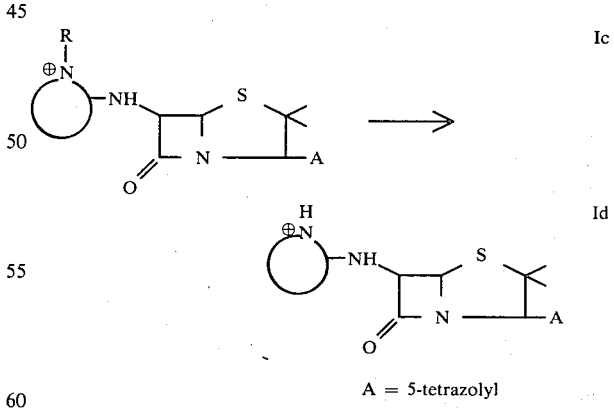

A = 5-tetrazolyl wherein R is —CH$_2$OCH$_3$, —CH$_2$OCOCH$_3$ or the like. According to the above scheme, Ic→Id, the group R is conveniently removed by treating Ic in anhydrous sulpholane at 20° C. with a 3- to 4-fold molar ration of I Si(CH$_3$)$_3$, followed by hydrolysis to yield Id. A representative example is included below. The reaction may schematically be shown as follows:

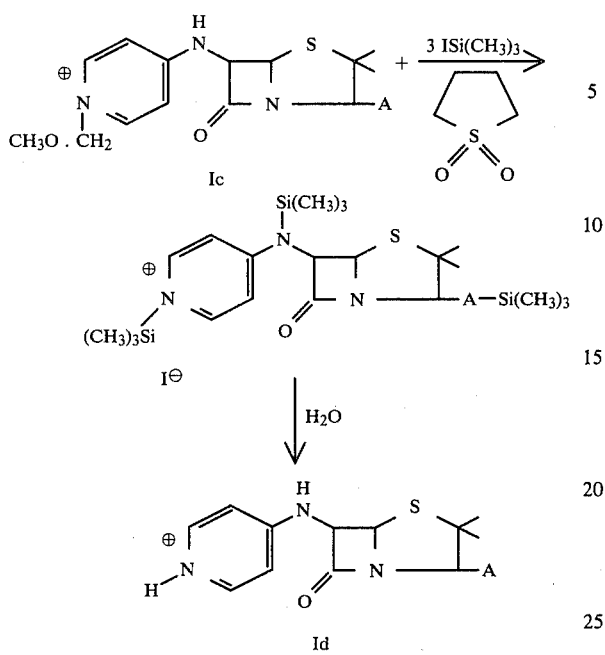

The product Id is then isolated directly from the reaction solution at pH 7 by preparative reverse phase HPLC as already described.

IDENTIFICATION OR REAGENTS

The necessary electrophilic, N-heterocyclic reagents 2 and 3 are known and commercially available or may be prepared according to known procedures; see, for example: *Advances in Heterocyclic Chemistry*, pp. 1–56, Vol. 3 (1964) and pp. 71–121, Vol. 22 (1978); Academic Press. The following list representatively illustrates such reagents.

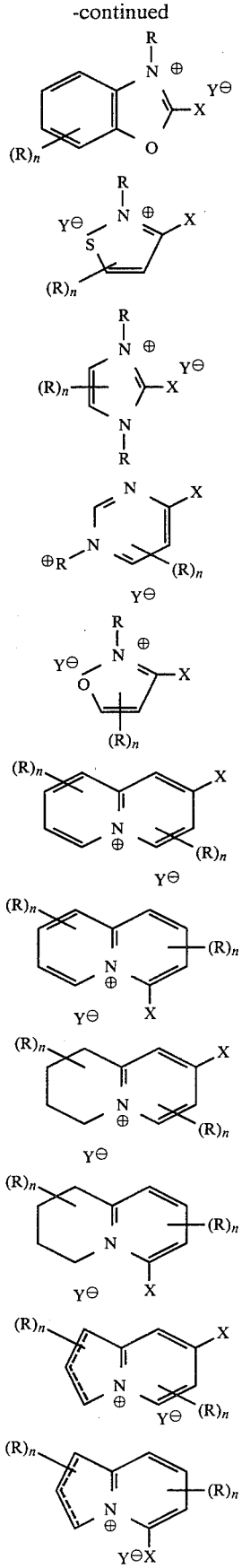

-continued

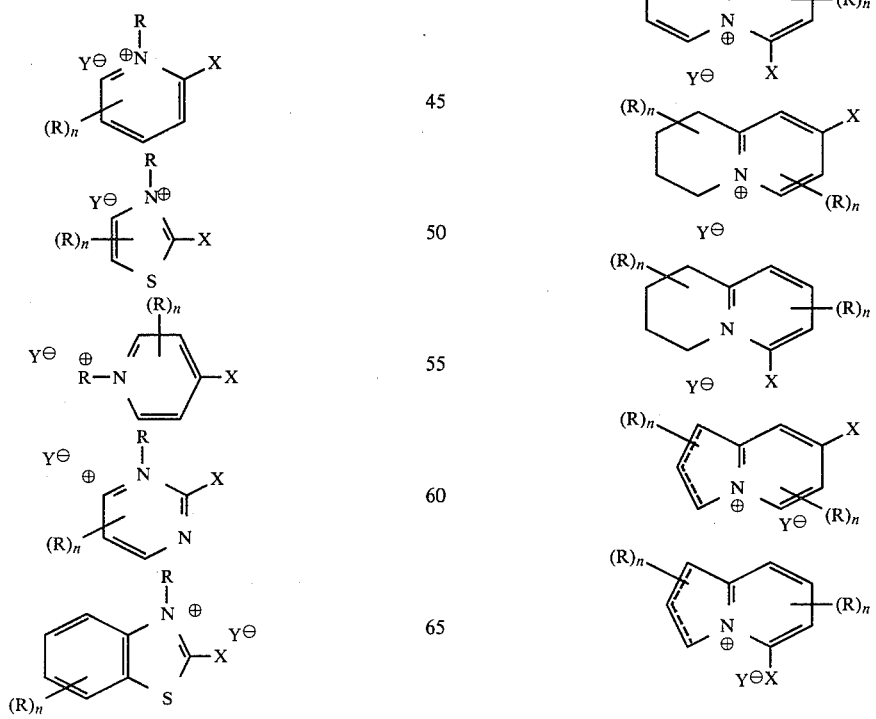

wherein all symbols have previously been defined; the dotted line indicates both saturated and unsaturated rings.

Relative to the above-listed reagents, the preferred values for the radical R which is directly attached to the ring nitrogen atom are: hydrogen; loweralkyl having from 1-10 carbon atoms; substituted alkyl wherein the substituent is chloro, fluoro, hydroxyl, alkoxyl, substituted alkoxy, carboxyl, amino, sulfo, and mono- and dialkylamino wherein each alkyl has 1-6 carbon atoms; phenylalkyl (alkyl moiety having 1-6 carbon atoms) and substituted phenylalkyl wherein the substituents are selected from chloro, fluoro, carboxyl, amino, hydroxyl, lower alkoxyl having from 1-6 carbon atoms, sulfo,

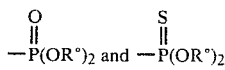

($R^°$ is hydrogen or alkyl having 1-6 carbon atoms). The quinolizinium and indolizinium examples are a special category of preferred values of R, in that R is there an integral part of a bicyclic system (R', defined above).

The preferred values for the other, non-position-specific ring substituent R are: chloro, fluoro, carboxyl and loweralkyl having from 1-6 carbon atoms; substituted lower alkyl wherein the substituent is carboxyl, cyano, alkoxyl having 1-6 carbon atoms, phenyl, and phenyloxy; the preferred value for n is 0 or 1. The preferred leaving group X is chloro or fluoro.

The compounds of the present invention (I) are valuable antibiotics active against various gram-positive and gram-negative bacteria and accordingly find utility in human and veterinary medicine. Representative pathogens which are sensitive to antibiotics I include: *Staphyloccus aureus, Escherichia coli, Klebsiella pneumoniae, Bacillus subtilis, Salmonella typhosa, Pseudomonas* and *Bacterium proteus.* The antibacterials of the invention are not limited to utility as medicaments; they may be used in all manner of industry, for example: additives to animal feed, preservation of food, disinfectants, and in other industrial systems where control of bacterial growth is desired. For example, they may be employed in aqueous compositions in concentrations ranging from 0.1 to 100 parts of antibiotic per million parts of solution in order to destroy and inhibit the growth of harmful bacteria on medical and dental equipment and as bactericides in industrial applications, for example in water-based paints and in the white water of paper mills to inhibit the growth of harmful bacteria.

The products of this invention may be used in any of a variety of pharmaceutical preparations. They may be employed in capsule, powder form, in liquid solution, or in suspension. They may be administered by a variety of means; those of principal interest include: orally, topically or parenterally by injection (intravenously or intramuscularly).

Such tablets and capsules, designed for oral administration, may be in unit dosage form, and may contain conventional excipients, such as binding agents, for example, syrup, acacia, gelatin, sorbitol, tragacanth, or polyvinylpyrrolidone; fillers, for example, lactose, sugar, cornstarch, calcium phosphate, sorbitol, or glycine; lubricants, for example, magnesium stearate, talc, polyethylene glycol, silica; disintegrants, for example, potato starch; or acceptable wetting agents such as sodium lauryl sulphate. The tablets may be coated according to methods well known in the art. Oral liquid preparations may be in the form of aqueous or oily suspensions, or solutions, or they may be presented as a dry product for reconstitution with water or other suitable vehicle before use. Such liquid preparations may contain conventional additives such as suspending agents, for example, sorbitol, methyl cellulose, glucose/sugar syrup, gelatin, hydroxyethylcellulose, or carboxymethyl cellulose. Suppositories will contain conventional suppository bases, such as cocoa butter or other glycerides.

Compositions for injection, the preferred route of delivery, may be prepared in unit dosage form in ampules, or in multidose containers. The compositions may take such forms as suspensions, solutions, or emulsions in oily or aqueous vehicles, and may contain formulatory agents such as suspending, stabilizing and/or dispersing agents. Alternatively, the active ingredient may be in powder form for reconstitution, at the time of delivery, with a suitable vehicle, such as sterile water.

The compositions may also be prepared in suitable forms for absorption through the mucous membranes of the nose and throat or bronchial tissues and may conveniently take the form of liquid sprays or inhalants, lozenges, or throat paints. For medication of the eyes or ears, the preparation may be presented in liquid or semi-solid form. Topical applications may be formulated in hydrophobic or hydrophilic bases as ointments, creams, lotions, paints, or powders.

The dosage to be administered depends to a large extent upon the condition and size of the subject being treated as well as the route and frequency of administration—the parenteral route by injection being preferred for generalized infections. Such matters, however, are left to the routine discretion of the therapist according to principles of treatment well known in the antibiotic art. In general, a daily dosage consists of from about 5 to about 600 mg of active ingredient per kg. of body weight of the subject in one or more treatments per day. A preferred daily dosage for adult humans lies in the range of from about 10 to 240 mg. of active ingredient per kg. of body weight. Another factor influencing the precise dosage regimen, apart from the nature of the infection and peculiar identity of the individual being treated, is the molecular weight of the chosen species of this invention (I).

The compositions for human delivery per unit dosage, whether liquid or solid, may contain from 0.1% to 99% of active material, the preferred range being from about 10-60%. The composition will generally contain from about 15 mg. to about 1500 mg. of the active ingredient; however, in general, it is preferable to employ a dosage amount in the range of from about 250 mg to 1000 mg. In parenteral administration, the unit dosage is usually the pure zwitterionic compound in sterile water solution or in the form of a soluble powder intended for solution. The pH of such solutions typically will correspond to the zwitterionic point; however, consideration of individual properties of solubility and stability may require such aqueous solutions to have a pH other than that of the zwitterionic point, for example in the range of 5.5 to 8.2.

The following examples, illustrate but do not limit the product, process, compositional or method of treatment aspects of the present invention. All reaction temperatures are in °C.

Finally, attention is drawn to a co-pending U.S. patent application Ser. No. 34,035 of John Hannah which was filed Apr. 27, 1979. Such pending Hannah application is directed to 7-N-heterocyclylcephalosporins which are in analogy to the penicillin compounds of the present invention. Thus, to the extent that the identified application recites common procedures and starting materials, it is hereby incorporated by reference.

EXAMPLE 1

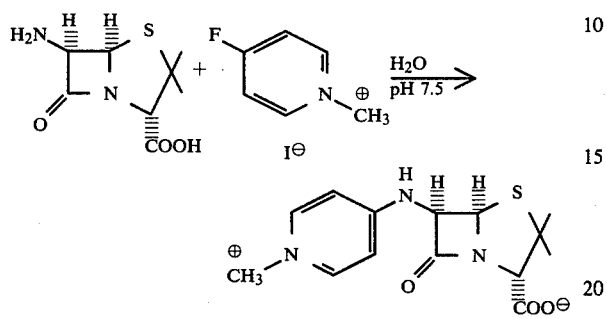

With the end point set at pH 7.5, aqueous NaOH (2.5 N) is added from an automatic burette to a magnetically stirred suspension of 6-aminopenicillanic acid (200 mg., 0.925 mmole) in distilled deionized water (3.0 ml) at 25° C. The initial pH is 3.7; the solid readily dissolves forming a clear solution. The reagent 2, 4-fluoro-1-methylpyridinium iodide (265 mg., 1.11 mmole), is added to the above solution, dissolving rapidly and causing a slow response from the automatic burette to maintain pH 7.5. The progress of the reaction is monitored by analytical HPLC(Waters Associates; $C_{18}$ ODS reverse phase column with aqueous 10% THF as the mobile phase), using a U.V. (254 nm) detector. After 1 hour at room temperature the reaction is complete. The solution is adjusted to pH 6.2 and put on a 3×45 cm. column of Amberlite XAD-2 resin, prepared in distilled deionized water, eluting with the same solvent, water. With the flow rate set at 2 drops per second individual fractions of 200 drop each are collected again using a U.V. monitor and analytical HPLC to locate the desired product. The eluting solvent is changed to aqueous 5% tetrahydrofuran at fraction 65. The product is found in fractions 105–117 which are combined and lyophylized to yield an off-white powder (262 mg).

IR: β-lactam at 1765 cm$^{-1}$
U.V.: $\lambda_{max}$(H$_2$O): 194, 212, 283 nm (ε 17,310, 21,740 and 23,050 respectively.)
NMR (300 MHz): δ1.40 (s, 3H, CH$_3$); 1.50 (s, 3H, CH$_3$); 3.85 (s, 3H, N$^\oplus$—CH$_3$); 4.19 (s, 1H, H$_3$); 5.38 (d, 1H, J=4 Hz, H$_5$); 5.64 (d, 1H, J=4 Hz, H$_6$); 6.92 (d, 2H, J=5 Hz, H$_{3'}$+H$_{5'}$); 8.01 (broad s, 2H, H$_{2'}$+H$_{6'}$).

EXAMPLE 1a

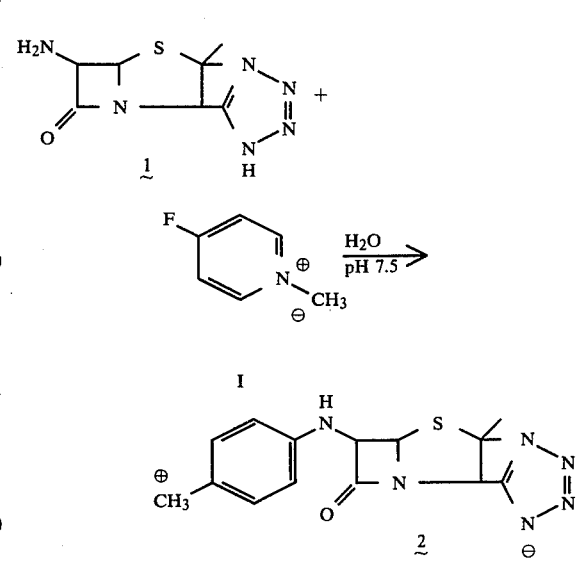

Following the procedure of Example 1 except substituting an equivalent amount of starting material 1 for the 6-aminopenicillanic acid of Example 1, there is obtained product 2.

EXAMPLE 2

Following the procedure described in the foregoing text and Examples, the following compounds listed in Table I are obtained. In Table I, appropriate remarks are entered to signal any departure from established procedure. Also listed under "Remarks" in Table I are the necessary reagents.

TABLE I

| Compound | R' | Remarks |
|---|---|---|
| 1 | ⊕N-pyridinium-CH$_2$-cyclopropyl (4-CH$_3$) | ⊕N-pyridinium-CH$_2$-cyclopropyl (4-F) I$^\ominus$ |
| 2 | ⊕N-pyridinium-CH$_2$CH$_3$ (4-CH$_3$) | ⊕N-pyridinium-CH$_2$CH$_3$ (4-F) BF$_4^\ominus$ |

TABLE I-continued

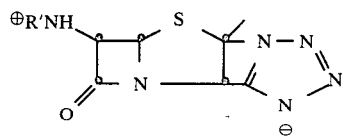

| Compound | R' | | Remarks |
|---|---|---|---|
| 3 | 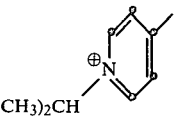 (CH₃)₂CH | 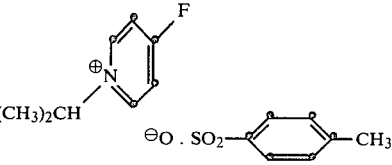 (CH₃)₂CH  ⊖O.SO₂—⟨⟩—CH₃ | |
| 4 | 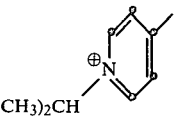 CH₂=CH.CH₂ | 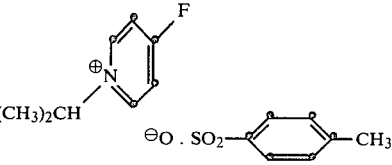 CH₂=CHCH₂  ⊖O.SO₂—⟨⟩—CH₃ | |
| 5 | 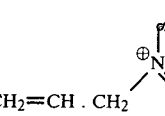 CH₃  CH₃ | 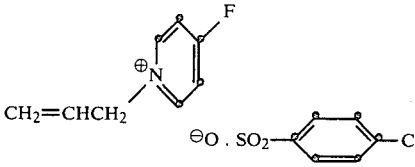 CH₃  CH₃  BF₄⊖ | |
| 6 | 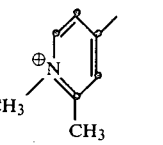 CH₃ CH₃  CH₃ | 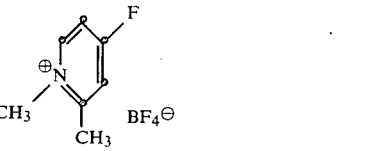 CH₃  CH₃  CH₃  ⊖PF₆ | |
| 7 | 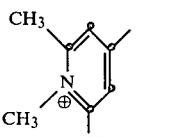 CH₃.O.CH₂ | 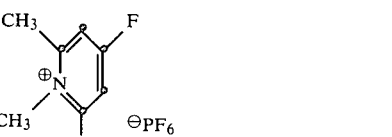 CH₃OCH₂  Br⊖ | |
| 8 | 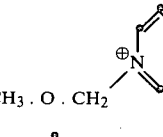 H | | From Compound 7 by reaction with (a) ISi(CH₃)₃ then (b) H₂O. |
| 9 | 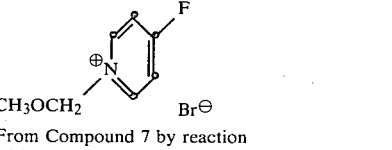 CH₃  COOCH₃ | 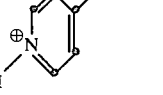 CH₃  COOCH₃  BF₄⊖ | |
| 10 | 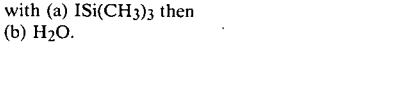 CH₃  COO⊖M⊕ | | from compound 9 by hydrolysis at pH = 9 then titration to pH = 7 |
| 11 | 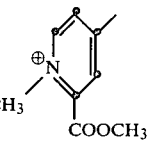 CH₃  COOCH₃ | 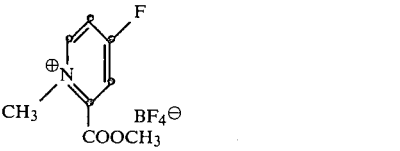 CH₃  COOCH₃  BF₄⊖ | |
| 12 | 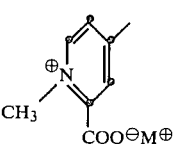 CH₃  COO⊖M⊕ | | from compound 11 by hydrolysis at pH = 9 then titration to pH = 7 |

TABLE I-continued

[Structure shown at top: ⊕R'NH—[β-lactam with S]—C(CH3)—N=N-N=N tetrazole with N⊖, and C=O, N in the ring]

| Compound | R' | | Remarks |
|---|---|---|---|
| 13 | [4-methylpyridinium-N-CH2COOCH3] | [5-chloro-4-methylpyridinium-N-CH2COOCH3, Br⊖] | |
| 14 | [4-methylpyridinium-N-CH2COO⊖ M⊕] | | from compound 13 by hydrolysis at pH = 9 then titration at pH = 7 |
| 15 | [3-chloro-4-methyl-N-methylpyridinium] | [3-chloro-4-methyl-5-fluoro-N-methylpyridinium, BF4⊖] | |
| 16 | [3-methoxy-4-methyl-N-methylpyridinium] | [3-methoxy-4-methyl-5-fluoro-N-methylpyridinium, BF4⊖] | |
| 17 | [4-methyl-N-phenylpyridinium] | [4-methyl-5-fluoro-N-phenylpyridinium, ⊖OSO2-C6H4-CH3] | |
| 18 | [4-methyl-N-benzylpyridinium] | [4-methyl-5-fluoro-N-benzylpyridinium, Br⊖] | |
| 19 | [4-methyl-N-hydroxypyridinium] | [4-methyl-5-fluoro-N-oxidopyridinium, ⊖O] | |
| 20 | [4-methyl-N-methoxypyridinium] | [4-methyl-5-fluoro-N-methoxypyridinium, BF4⊖] | |
| 21 | [4-methyl-N-aminopyridinium] | | from compound 8. by reaction with H2N.O.SO3H |
| 22 | [4-methyl-N-methyl-3-sulfonatopyridinium SO3⊖M⊕] | [4-methyl-5-fluoro-N-methyl-3-(methylsulfonate)pyridinium SO3CH3, ⊖BF4⊖] | and subsequent hydrolysis at pH = 9 and titration to pH = 7 |

TABLE I-continued
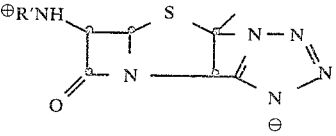
| Compound | R' | | Remarks |
|---|---|---|---|
| 23 | 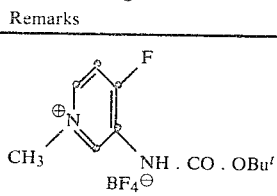 | 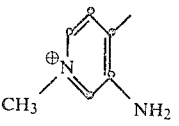 and subsequent cleavage by CF₃COOH | |
| 24 | 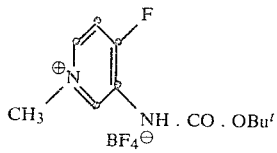 | 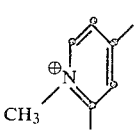 and subsequent cleavage by CF₃COOH | |
| 25 | 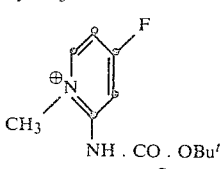 | from compound 16 by reaction with (a) ISi(CH₃)₃ then (b)H₂O | |
| 26 | 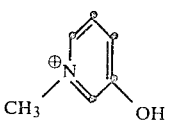 | 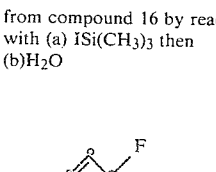 | |
| 27 | 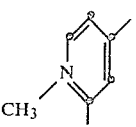 | from compound 26 by reaction with (a) ISi(CH₃)₃; (b) H₂O; then M⊕OH⊖ to pH 7 isolating the product as the cephem —COO⊖M⊕ | |
| 28 | 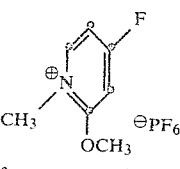 | 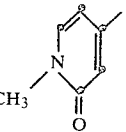 | |
| 29 | 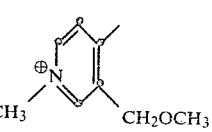 | 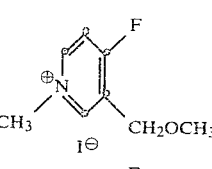 | |
| 30 | 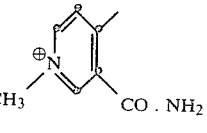 | 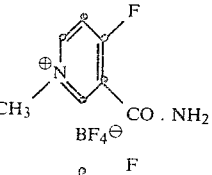 | |
| 31 | 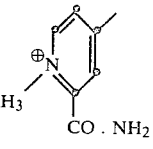 | 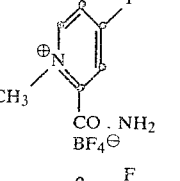 | |

TABLE I-continued

[Structure: ⊕R'NH-β-lactam-thiazolidine-tetrazole core structure shown at top]

| Compound | R' | Remarks |
|----------|----|---------|

32: [4-methylpyridinium-CH₂-C(=O)-CH₃] / [4-chloropyridinium-CH₂-C(=O)-CH₃] Br⊖

33: [4-methylpyridinium-CH₂-C(=O)-phenyl] / [4-chloropyridinium-CH₂-C(=O)-phenyl] Br⊖

34: [4-methylpyridinium-CH₂-furan] / [4-chloropyridinium-CH₂-furan] Br⊖

35: [4-methylpyridinium-CH(COOCH₃)-phenyl] / [4-chloropyridinium-CH(COOCH₃)-phenyl] Br⊖

36: [4-methylpyridinium-CH(COO⊖M⊕)-phenyl] — from compound 35 by hydrolysis at pH 9, then titration to pH 7

37: [M⊕⊖OOC-phenyl-CH₂-pyridinium] / [CH₃OOC-phenyl-CH₂-(4-fluoropyridinium)] Br⊖ and subsequent hydrolysis at pH = 9 and titration to pH = 7

38: [HO-phenyl-CH₂-(4-methylpyridinium)] / from CH₃CO·O-phenyl-CH₂-(4-fluoropyridinium) Br⊖ and subsequent hydrolysis at pH 9 and titration to pH 7

39: [3,4-dimethoxyphenyl-CH₂-(4-methylpyridinium)] / [3,4-dimethoxyphenyl-CH₂-(4-fluoropyridinium)] Br⊖

40: [phenyl-CH₂-(2-COOCH₃, 4-methylpyridinium)] / [phenyl-CH₂-(2-COOCH₃, 4-fluoropyridinium)] Br⊖

TABLE I-continued

Structure: ⊕R'NH—[β-lactam with S]—C(CH₃)—tetrazole (N⁻)

| Compound | R' | | Remarks |
|---|---|---|---|
| 41 | benzyl-(2-COO⁻M⁺)-4-methylpyridinium | | from compound 40 by hydrolysis at pH 9 then titration to pH 7 |
| 42 | 3-(CH₃SO)-benzyl-(4-methylpyridinium) | 3-(CH₃SO)-benzyl-(2-fluoropyridinium) Br⁻ | |
| 43 | N-methyl-2-methylpyridinium | N-methyl-2-fluoropyridinium I⁻ | |
| 44 | N-methyl-2,4-dimethylpyridinium | N-methyl-2-fluoro-4-methylpyridinium I⁻ | by reaction in anhydrous DMF with diethylisopropylamine as base |
| 45 | N-methyl-2-(CH₃OOC)-6-methylpyridinium | N-methyl-2-(CH₃OOC)-6-fluoropyridinium BF₄⁻ | |
| 46 | N-methyl-2-(M⁺⁻OOC)-6-methylpyridinium | | from compound 45 by hydrolysis at pH 9 then titration to pH 7 |
| 47 | N-methyl-3-(CH₃OOC)-6-methylpyridinium | N-methyl-3-(CH₃OOC)-6-fluoropyridinium BF₄⁻ | |
| 48 | N-methyl-3-(M⁺⁻OOC)-6-methylpyridinium | | from compound 47 by hydrolysis at pH 9 then titration to pH 7 |
| 49 | N-methyl-3-(H₂NOC)-6-methylpyridinium | N-methyl-3-(H₂NOC)-6-fluoropyridinium BF₄⁻ | |

TABLE I-continued

[Structure: ⊕R'NH—[β-lactam with S]—N—[CH(CH3)2]—tetrazole ring (N—N=N—N⊖)]

| Compound | R' | Remarks |
|---|---|---|
| 50 | 2-methyl-3-chloro-N-methylpyridinium (⊕) | BF$_4^\ominus$; 2-fluoro-3-chloro-N-methylpyridinium (⊕) |
| 51 | 2-methyl-4-chloro-N-methylpyridinium (⊕) | BF$_4^\ominus$; 2-fluoro-4-chloro-N-methylpyridinium (⊕) |
| 52 | 2,6-dimethyl-N-methylpyridinium (⊕) | BF$_4^\ominus$; 2-fluoro-6-methyl-N-methylpyridinium (⊕) |
| 53 | 2-methyl-N-(CH$_3$·O·CH$_2$)pyridinium (⊕) | Br$^\ominus$; 2-fluoro-N-(CH$_3$·O·CH$_2$)pyridinium (⊕) |
| 54 | 2-methylpyridinium (⊕, N—H) | from compound 53 by reaction with (a) ISi(CH$_3$)$_3$ then (b) H$_2$O |
| 55 | 2-methyl-N-hydroxypyridinium (⊕) | 2-fluoro-N-oxidopyridinium (⊕, O$^\ominus$) |
| 56 | 2-methyl-N-methoxypyridinium (⊕) | BF$_4^\ominus$; 2-fluoro-N-methoxypyridinium (⊕) |
| 57 | 2-methyl-N-aminopyridinium (⊕, NH$_2$) | from compound 54 by reaction with H$_2$NO·SO$_3$H |
| 58 | 2-methyl-N-(CHOOC·CH$_2$)pyridinium (⊕) | Br$^\ominus$; 2-fluoro-N-(CH$_3$OOC·CH$_2$)pyridinium (⊕) |
| 59 | 2-methyl-N-(M$^\oplus$OOC·CH$_2$)pyridinium (⊕) | from compound 58 by hydrolysis at pH 9 then titration to pH 7 |

TABLE I-continued

[Structure: ⊕R'NH-β-lactam-CH-tetrazole core]

| Compound | R' | | Remarks |
|---|---|---|---|

60: R' = 2-methyl-5-amino-pyridinium (H₂N-, N⁺-CH₃); Remarks: BF₄⊖ salt of 2-methyl-6-fluoro-5-(Buᵗ O·CONH)-pyridinium, and subsequent cleavage by CF₃·COOH

61: R' = 1,2-dimethyl-5-sulfonato-pyridinium (M⊕⊖O₃S-); Remarks: BF₄⊖ salt of 1,2-dimethyl-6-chloro-5-(CH₃O-SO₂-)-pyridinium, and subsequent hydrolysis at pH 9 and titration to pH 7

62: R' = N-benzyl-2-methylpyridinium (PhCH₂-N⊕); Remarks: Br⊖ salt of N-benzyl-2-fluoropyridinium

63: R' = N-(4-hydroxybenzyl)-2-methylpyridinium (HO-C₆H₄-CH₂-N⊕); Remarks: From CH₃COO-C₆H₄-CH₂-N⊕-2-fluoropyridinium Br⊖, and subsequent hydrolysis at pH 9 and titration to pH 7

64: R' = N-(4-methoxycarbonylbenzyl)-2-methylpyridinium (CH₃OOC-C₆H₄-CH₂-N⊕); Remarks: CH₃OOC-C₆H₄-CH₂-N⊕-2-fluoropyridinium Br⊖

65: R' = N-(4-carboxylatobenzyl)-2-methylpyridinium (M⊕⊖OOC-C₆H₄-CH₂-N⊕); Remarks: from compound 64 by hydrolysis at pH 9 then titration to pH 7

TABLE I-continued
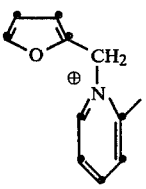
| Compound | R' | Remarks |
|---|---|---|
| 66 | 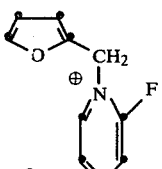 | 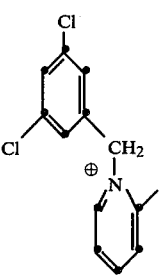 Br⊖ |
| 67 | 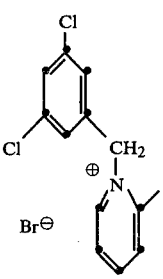 | 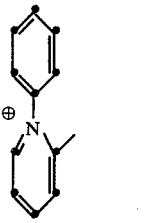 Br⊖ |
| 68 | 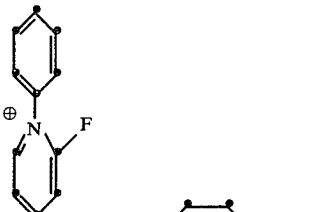 | 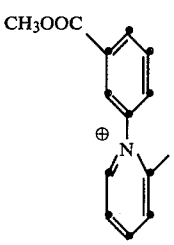 |
| 69 | 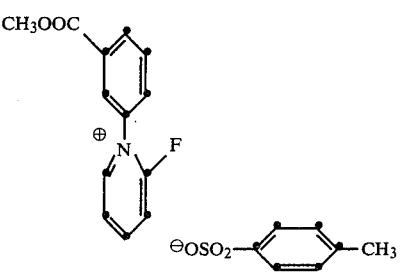 | 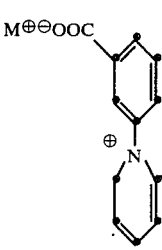 |
| 70 | 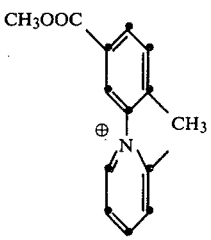 | from compound 69 by hydrolysis at pH 9 then titration to pH 7 |
| 71 | 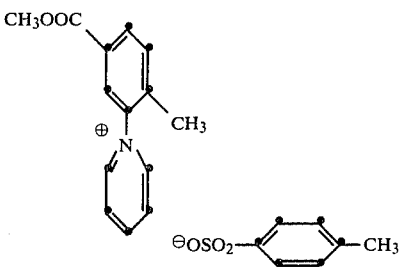 | |

TABLE I-continued
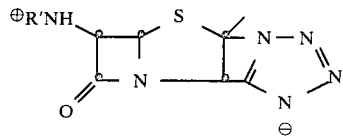
| Compound | R' | | Remarks |
|---|---|---|---|
| 72 | 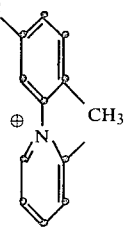 | | from compound 71 by hydrolysis at pH 9 then titration to pH 7 |
| 73 | 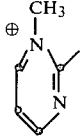 | BF₄⁻ 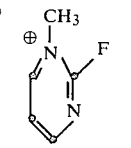 | |
| 74 | 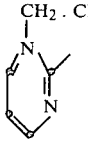 | BF₄⁻ 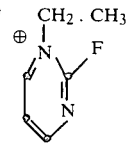 | |
| 75 | 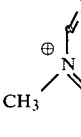 | 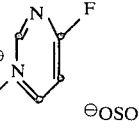 | |
| 76 | 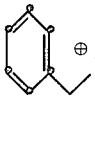 | 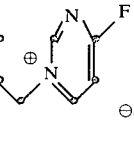 | |
| 77 | 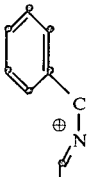 | 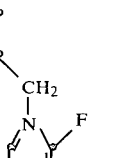 | |
| 78 |  | 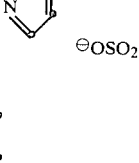 | |
| 79 | 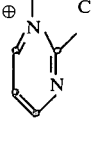 | BF₄⁻ 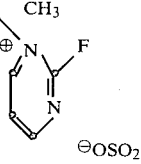 | |

TABLE I-continued

| Compound | R' | Remarks |
|---|---|---|
| 80 | 4-phenyl-3-methyl-2-methylthiazolium | 4-phenyl-3-methyl-2-fluorothiazolium BF$_4^\ominus$ |
| 81 | 3-ethyl-4-methyl-2-methylthiazolium | 3-ethyl-4-methyl-2-fluorothiazolium BF$_4^\ominus$ |
| 82 | N-ethyl-substituted oxazine with phenyl | BF$_4^\ominus$, fluorinated analog |
| 83 | N-ethyl-substituted oxazine with CH$_3$ | BF$_4^\ominus$, fluorinated analog |
| 84 | N-ethyl-substituted thiazine | BF$_4^\ominus$, fluorinated analog |
| 85 | 1,3-dimethyl-2-methylbenzimidazolium | 1,3-dimethyl-2-fluorobenzimidazolium BF$_4^\ominus$ |
| 86 | methyl ester 1,3-dimethyl-2-methylbenzimidazolium carboxylate | methyl ester 1,3-dimethyl-2-fluorobenzimidazolium carboxylate BF$_4^\ominus$ |
| 87 | M$^\oplus \ominus$OOC- 1,3-dimethyl-2-yl-benzimidazolium | from compound 86 by hydrolysis at pH 9 then titration to pH 7 |

TABLE I-continued
| Compound | R' | | Remarks |
|---|---|---|---|
| 88 | 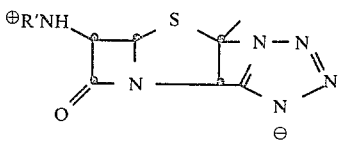 | 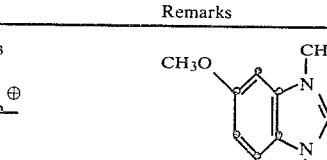 BF$_4^\ominus$ | |
| 89 | 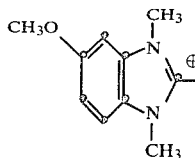 | 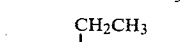 BF$_4^\ominus$ | |
| 90 | 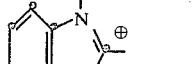 | 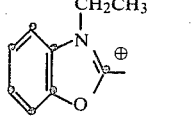 BF$_4^\ominus$ | |
| 91 | 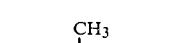 | 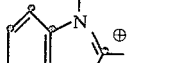 BF$_4^\ominus$ | |
| 92 | 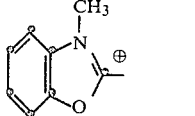 | 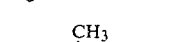 $^\ominus$OSO$_2$-C$_6$H$_4$-CH$_3$ | |
| 93 | 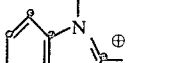 | 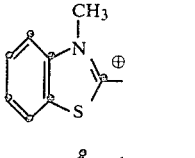 $^\ominus$OSO$_2$-C$_6$H$_4$-CH$_3$ | |
| 94 |  |  Br$^\ominus$ | |
| 95 | 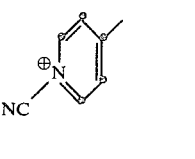 |  Br$^\ominus$ | |
| 96 |  | 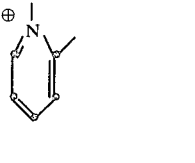 ClO$_4^\ominus$ | |
| 97 |  | 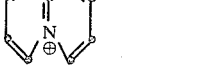 $^\ominus$OSO$_2$-C$_6$H$_4$-CH$_3$ | |

TABLE I-continued

Structure: ⊕R'NH-[β-lactam]-S-C(CH₃)₂-CH₂-tetrazolate

| Compound | R' | Remarks |
|---|---|---|
| 98 | (methyl-pyridinium bicyclic) | (fluoro-pyridinium bicyclic), ⊖OSO₂-C₆H₄-CH₃ |
| 99 | CH₃OCH₂-N⊕(methylpyrimidinium) | CH₃OCH₂-N⊕(fluoropyrimidinium), Br⊖ |
| 100 | H-N⊕(fluoropyrimidinium) | prepared from compound 98 by reaction with (a) ISi(CH₃)₃ then (b) H₂O |
| 101 | NC-C₆H₄-CH₂-N⊕(methylpyridinium) | NC-C₆H₄-CH₂-N⊕(fluoropyridinium), Br⊖ |
| 102 | (CH₃)₂N-C₆H₄-CH₂-N⊕(methylpyridinium) | (CH₃)₂N-C₆H₄-CH₂-N⊕(fluoropyridinium), Br⊖ |
| 103 | C₆H₅-CH₂-CH₂-N⊕(methylpyridinium) | C₆H₅-CH₂-CH₂-N⊕(fluoropyridinium), ⊖OTs |
| 104 | Cl₃C·CH₂·O·CH₂-N⊕(methylpyridinium) | Cl₃C·CH₂·OCH₂-N⊕(fluoropyridinium), Br⊖ |
| 105 | F₃C·CH₂·O·CH₂-N⊕(methylpyridinium) | F₃C·CH₂·O·CH₂-N⊕(fluoropyridinium), Br⊖ |
| 106 | C₆H₅-O-N⊕(methylpyridinium) | C₆H₅-O-N⊕(fluoropyridinium), Br⊖ |

EXAMPLE 3

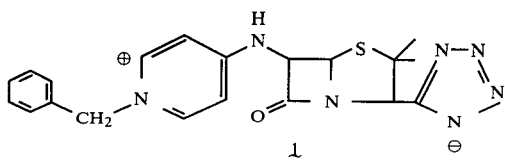

Preparation of Pharmaceutical Compositions

One such unit dosage form comprises a blend of 120 mg of 1 with 20 mg of lactose and 5 mg of magnesium stearate which is placed in a No. 3 gelatin capsule. Similarly, by employing more of the active ingredient and less lactose, other dosage forms can be prepared; should it be necessary to mix more than 145 mg. of ingredients together, larger capsules may be employed. Equivalently, compressed tablets and pills can be prepared. The following examples are further illustrative of the preparation of pharmaceutical formulations:

| TABLET | PER TABLET |
|---|---|
| Compound 1 | 125 mg. |
| Dicalcium Phosphate | 200 mg. |
| Cornstarch, U.S.P. | 6 mg. |
| Lactose, U.S.P. | 200 mg. |
| Magnesium Stearate | 270 mg. |

The above ingredients are combined and the mixture is compressed into tablets, approximately 0.5 inch in diameter each weighing 800 mg.

What is claimed is:

1. A compound having the structural formula:

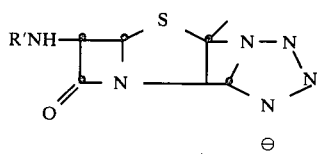

and the pharmaceutically acceptable salts and esters thereof wherein:

R' is selected from the group consisting of:

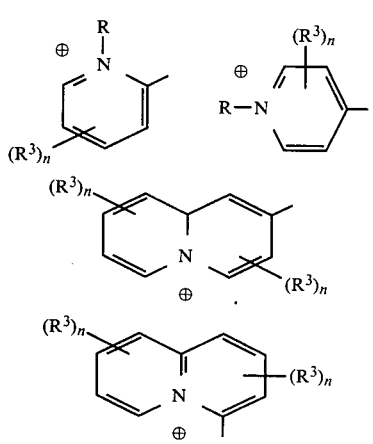

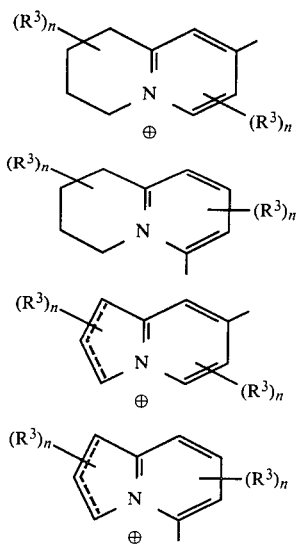

wherein the dotted line indicates both saturated and unsaturated rings; and wherein:

R is hydrogen, alkyl having from 1-6 carbon atoms, substituted alkyl having from 1-6 carbon atoms wherein the substituent is chloro, fluoro, hydroxyl, alkoxyl ($C_{1-6}$), carboxyl, amino, sulfo and mono- and dialkylamino wherein each alkyl has 1-6 carbon atoms substituted and unsubstituted phenylalklkyl and phenylalkenyl having 7-12 carbon atoms wherein the substituent is selected from chloro, fluoro, carboxyl, amino, cyano, hydroxyl and sulfo;

$R^3$ is chloro, fluoro, hydroxyl, carboxyl, sulfo, cyano, amino, mono- and dialkylamino, alkoxyl alkyl having from 1-6 carbon atoms, substituted alkyl having 1-6 carbon atoms wherein the substituent is carboxyl, cyano, alkoxyl having 1-6 carbon atoms, phenyl and phenyloxy;

n is an integer selected from 0 to 3.

2. A compound according to claim 1 wherein n is 0 or 1; and R is hydrogen or substituted or unsubstituted alkyl or phenylalkyl.

3. A compound according to claim 2 wherein R' is selected from the group consisting of:

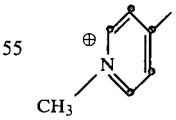 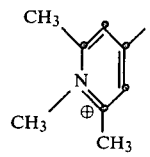

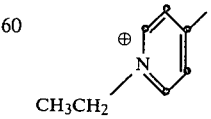 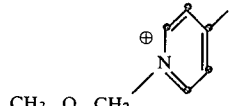

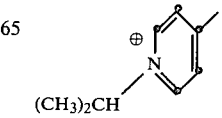 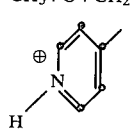

-continued
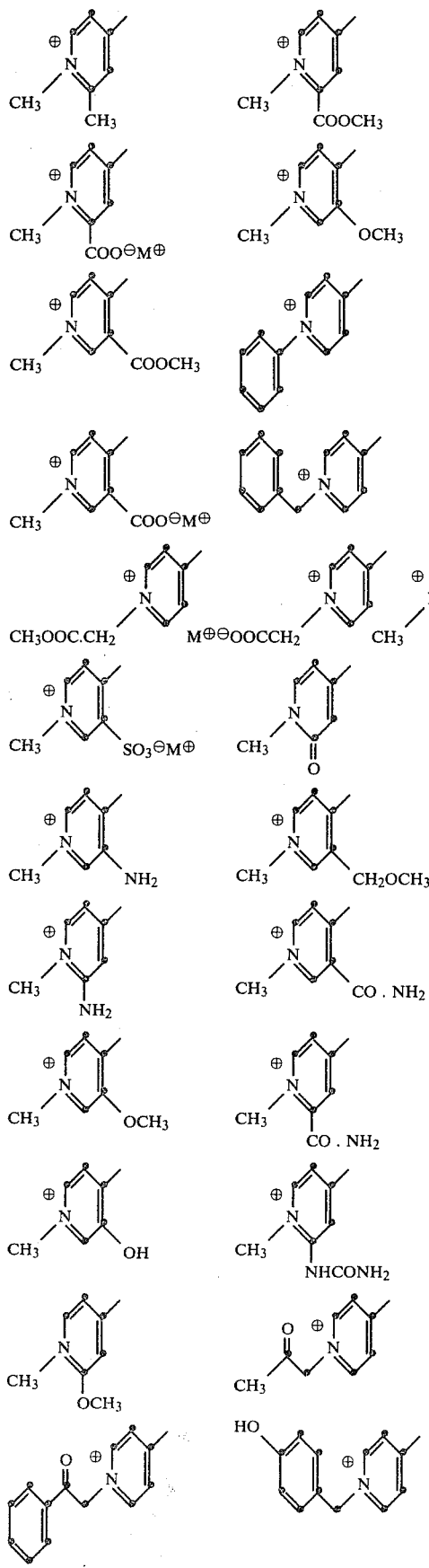
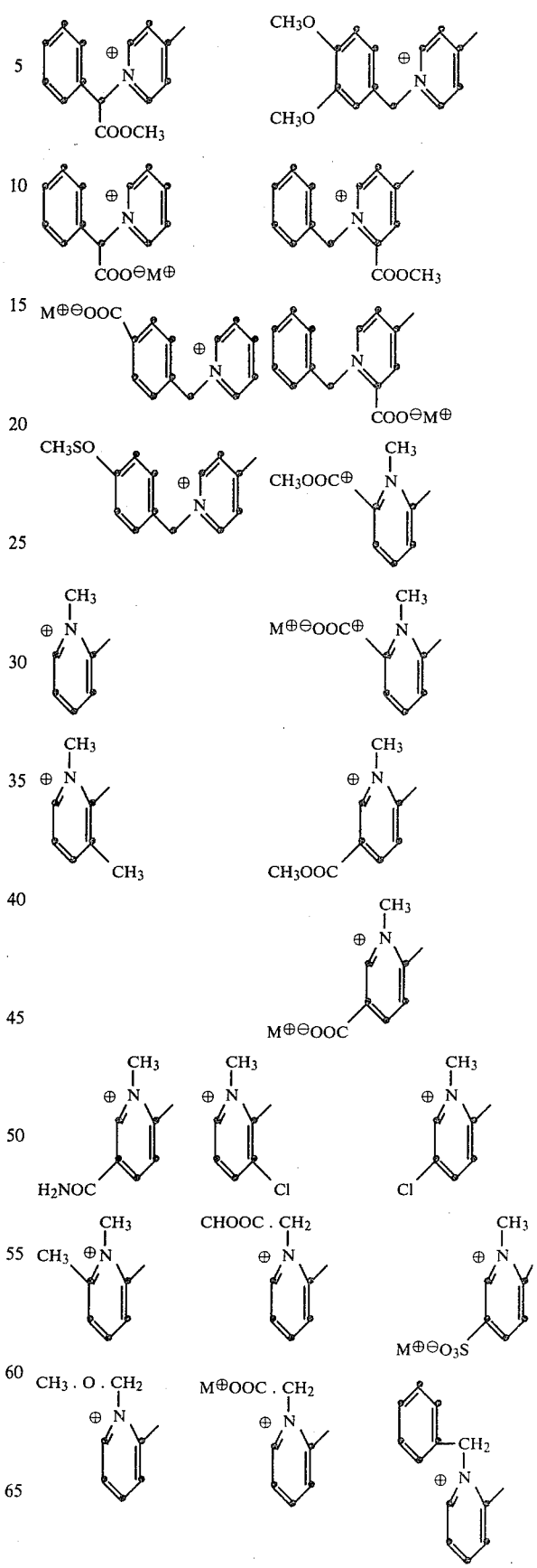

-continued
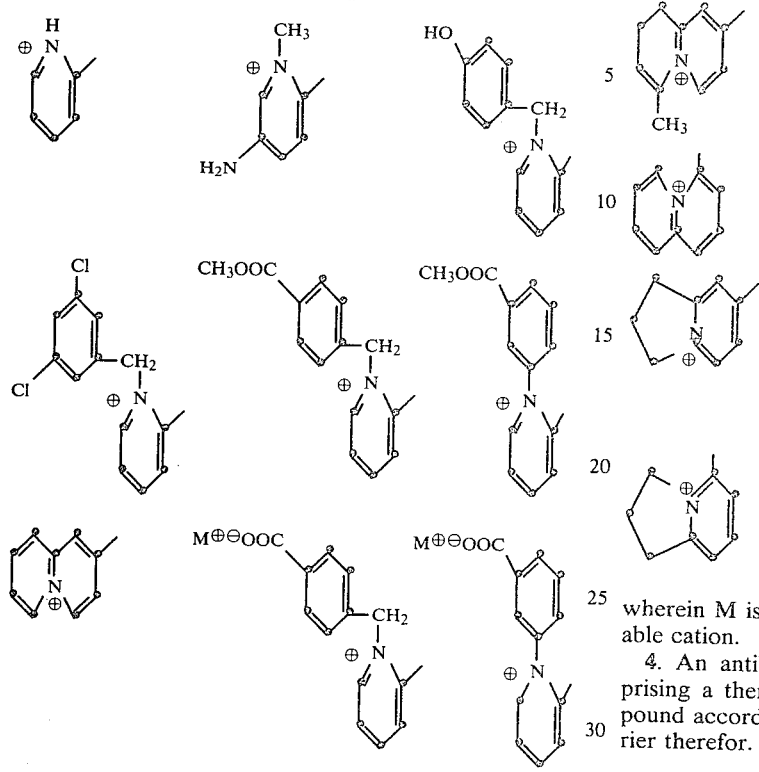
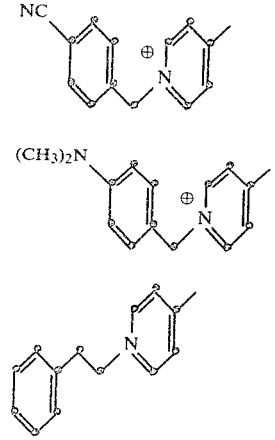
wherein M is hydrogen or a pharmaceutically acceptable cation.
4. An antibiotic pharmaceutical composition comprising a therapeutically, effective amount of a compound according to claim 1 and a pharmaceutical carrier therefor.
* * * * *